(12) United States Patent
Mehrkesh et al.

(10) Patent No.: US 10,168,080 B2
(45) Date of Patent: Jan. 1, 2019

(54) EUTECTIC MIXTURES OF IONIC LIQUIDS IN ABSORPTION CHILLERS

(71) Applicant: YAZAKI CORPORATION, Tokyo (JP)

(72) Inventors: Amirhossein Mehrkesh, Camarillo, CA (US); Stefan Maat, Camarillo, CA (US); George G. Tamas, Camarillo, CA (US)

(73) Assignee: YAZAKI CORPORATION, Tokyo (JP)

( * ) Notice: Subject to any disclaimer, the term of this patent is extended or adjusted under 35 U.S.C. 154(b) by 0 days.

(21) Appl. No.: 15/607,079

(22) Filed: May 26, 2017

(65) Prior Publication Data

US 2017/0343250 A1    Nov. 30, 2017

Related U.S. Application Data

(60) Provisional application No. 62/341,736, filed on May 26, 2016, provisional application No. 62/350,968, filed on Jun. 16, 2016.

(51) Int. Cl.

| | | |
|---|---|---|
| F25B 15/02 | (2006.01) | |
| C09K 5/00 | (2006.01) | |
| C09K 5/02 | (2006.01) | |
| C09K 5/04 | (2006.01) | |
| C07D 213/18 | (2006.01) | |
| C07D 233/54 | (2006.01) | |

(Continued)

(52) U.S. Cl.
CPC .......... *F25B 15/025* (2013.01); *C07D 213/18* (2013.01); *C07D 233/54* (2013.01); *C09K 5/00* (2013.01); *C09K 5/02* (2013.01); *C09K 5/04* (2013.01); *F25B 15/002* (2013.01); *F25B 15/006* (2013.01); *F25B 15/06* (2013.01); *C09K 5/047* (2013.01)

(58) Field of Classification Search
CPC ... C09K 5/00; C09K 5/02; C09K 5/04; C09K 5/047; F25B 15/025
USPC .......................................................... 252/74
See application file for complete search history.

(56) References Cited

U.S. PATENT DOCUMENTS

| | | | | |
|---|---|---|---|---|
| 8,506,839 B2 * | 8/2013 | Shiflett | .................. | C09K 5/047 252/67 |
| 2003/0185279 A1 * | 10/2003 | Wu | .......................... | G01K 5/12 374/159 |

(Continued)

FOREIGN PATENT DOCUMENTS

| | | |
|---|---|---|
| WO | 2010/117836 A1 | 10/2010 |
| WO | 2011/131606 A1 | 10/2011 |

OTHER PUBLICATIONS

Kick, M. et al., "Solid-liquid phase diagram of the two ionic liquids EMIMCI and BMIMCI", Fluid Phase Equilibria, vol. 338, Jan. 25, 2013, pp. 172-178.

(Continued)

*Primary Examiner* — Jane L Stanley
(74) *Attorney, Agent, or Firm* — Perkins Coie LLP; Viola T. Kung

(57) ABSTRACT

This invention relates to using a eutectic mixture of two ionic liquids, as an absorbent material in an absorption chiller. The invention provides an absorption chiller comprising a mixture of a refrigerant and an absorbent, and the absorbent is a eutectic mixture of two ionic liquids.

14 Claims, 5 Drawing Sheets

(51) Int. Cl.
*F25B 15/00* (2006.01)
*F25B 15/06* (2006.01)

(56) References Cited

U.S. PATENT DOCUMENTS

| | | | |
|---|---|---|---|
| 2004/0133058 A1* | 7/2004 | Arlt | B01D 3/36 |
| | | | 585/833 |
| 2007/0144186 A1* | 6/2007 | Shiflett | C09K 5/047 |
| | | | 62/112 |
| 2008/0028777 A1 | 2/2008 | Boesmann et al. | |
| 2010/0132384 A1* | 6/2010 | Shiflett | C09K 5/047 |
| | | | 62/112 |
| 2010/0326126 A1* | 12/2010 | Seiler | F25B 15/14 |
| | | | 62/497 |
| 2011/0247494 A1* | 10/2011 | Dinnage | B01D 53/1456 |
| | | | 95/92 |
| 2011/0265476 A1* | 11/2011 | Berger | F01K 13/02 |
| | | | 60/651 |
| 2012/0247144 A1* | 10/2012 | Seiler | C09K 5/047 |
| | | | 62/476 |
| 2013/0031930 A1 | 2/2013 | Seiler et al. | |
| 2013/0031931 A1 | 2/2013 | Seiler et al. | |
| 2013/0219949 A1* | 8/2013 | Seiler | C09K 5/047 |
| | | | 62/476 |
| 2013/0327084 A1* | 12/2013 | Shiflett | C09K 5/047 |
| | | | 62/478 |
| 2015/0007963 A1* | 1/2015 | Kalb | C09K 5/10 |
| | | | 165/104.19 |
| 2017/0343251 A1* | 11/2017 | Mehrkesh | F25B 15/06 |

OTHER PUBLICATIONS

Królikowska, M., "(Solid + liquid) and (liquid + liquid) phase equilibria of (IL + water) binary systems. The influence of the ionic liquid structure on mutual solubility", Fluid Phase Equilibria, vol. 361, Jan. 2014, pp. 273-281.
Prado, et al., "Chanpter 1: Applications of Ionic Liquids", In *Application, Purification, and Recovery of Ionic Liquids, 1st Edition*, Editors: Olga Kuzmina & Jason Hallett, © 2016 Elsevier, Feb. 25, 2016, pp. 1-58.
International Search Report dated Aug. 24, 2017 in International Application No. PCT/US2017/034799.

* cited by examiner

EUTECTIC MIXTURES OF IONIC LIQUIDS IN ABSORPTION CHILLERS

This application claims the benefit of U.S. Provisional Application Nos. 62/341,736, filed May 26, 2016, and 62/350,968, filed Jun. 16, 2016. The contents of the above-identified applications are incorporated herein by reference in their entireties.

TECHNICAL FIELD

This invention relates to an absorption chiller comprising a eutectic mixture of two ionic liquids as the absorbent material.

BACKGROUND

Absorption chillers are designed to generate cooling (chilling) effect by means of generating chilled water which can be used to extract heat from an air flow (e.g. in an air conditioning system). Absorption chillers create a chilling effect by going through a complete absorption-refrigeration cycle. The simultaneous heat and mass transfer of the refrigerant to and from its mixture with the absorbent is the main mechanism of producing the chilling effect in an absorption chiller. The absorbent in the system should have a great tendency towards the refrigerant by dissolving it readily under the operating conditions of the system. The absorption process will make it possible for the system to work at sub-atmospheric pressures (between 0.01-0.1 atm for a water-based absorption chiller) leading to the evaporation of the refrigerant at much lower temperatures than its normal boiling point.

In absorption chillers, the need for an electricity consuming part (i.e. a compressor) to pressurize the refrigerant is addressed through the use of an appropriate absorbent. Latent heat is consumed for the evaporation of the refrigerant, which provides a means of chilling. The low pressure in the evaporator provides the benefit of easy evaporation of the refrigerant (i.e. liquids evaporate easier at lower pressures), thereby making the system capable of producing a chilling effect at low temperatures. However, the very low pressure of the evaporator makes the condensation process of the vapor phase (in order for the cycle to be continued) more challenging. This is where an efficient absorbent is needed to thoroughly absorb the refrigerant vapor (which previously has been cooled by releasing latent heat to a cooling water stream) and to change it back into the liquid phase.

Like any other chemical/physical system, absorption chillers have their own drawbacks and limitations. Certain factors such as the crystallization of the absorbent in the system, or the heat loss from different compartments of the system, can make the system deviate from the ideal performance predicted by thermodynamic-based models. The benefits and drawbacks of conventional absorption chillers are described as follows.

Benefits of an Absorption Chiller:
- Low electricity cost—The only electricity consuming part in the system is a relatively small pump, which is used to circulate the absorbent-refrigerant mixture within the system. This fact makes absorption chillers an ideal choice for countries which do not have well developed infrastructures for the generation of electricity.
- It is a closed system in which almost no refrigerant (commonly water) is wasted.
- Ability to work in both dry and humid climates.

Drawbacks:
  Water-lithium bromide (LiBr) salt is a commonly used refrigerant-absorbent (working) pair in absorption chillers. LiBr is a very efficient absorbent for water refrigerant due to its high hygroscopicity. LiBr, which as a pure salt has a melting temperature of 552° C., can absorb water to a high enough degree such that it becomes completely dissolved in the water it has absorbed. [1]

However, absorption chillers working with LiBr absorbent can only operate within a relatively narrow range of the concentration of LiBr in water. The process is impaired if the solution of LiBr in water is either too concentrated or too dilute. On the one hand, a very low amount of water is insufficient to keep LiBr in the liquid phase due to the high melting point of LiBr (552° C.), causing the absorbent to crystallize out of the liquid working pair [2]. On the other hand, a very high amount of water (too dilute of a solution) will completely cover and solvate the $Li^+$ cations and $Br^-$ anions, disturbing the capability of the system to work continuously and efficiently. A narrow (~5%) change in LiBr concentration in the water (from ~57% LiBr/43% water in the diluted stream to ~62% LiBr/38% water in the concentrated stream) is typically required to produce an acceptable amount of cooling load while preventing the solution from being too concentrated or too dilute.

Another drawback of LiBr salt as an absorbent is its corrosiveness, necessitating the use of costly corrosion inhibitors and copper piping. Due to the corrosive nature of LiBr and the involved control procedures needed to avoid its crystallization within the system, there is a need for absorption chillers having less problematic absorbent materials compared with LiBr.

DETAILED DESCRIPTION OF THE INVENTION

The inventors have discovered that substituting a conventional absorbent with a eutectic mixture of two ionic liquids in an absorption chiller avoids the crystallization of the absorbent in the system and therefore improves its efficiency.

Figure 1:
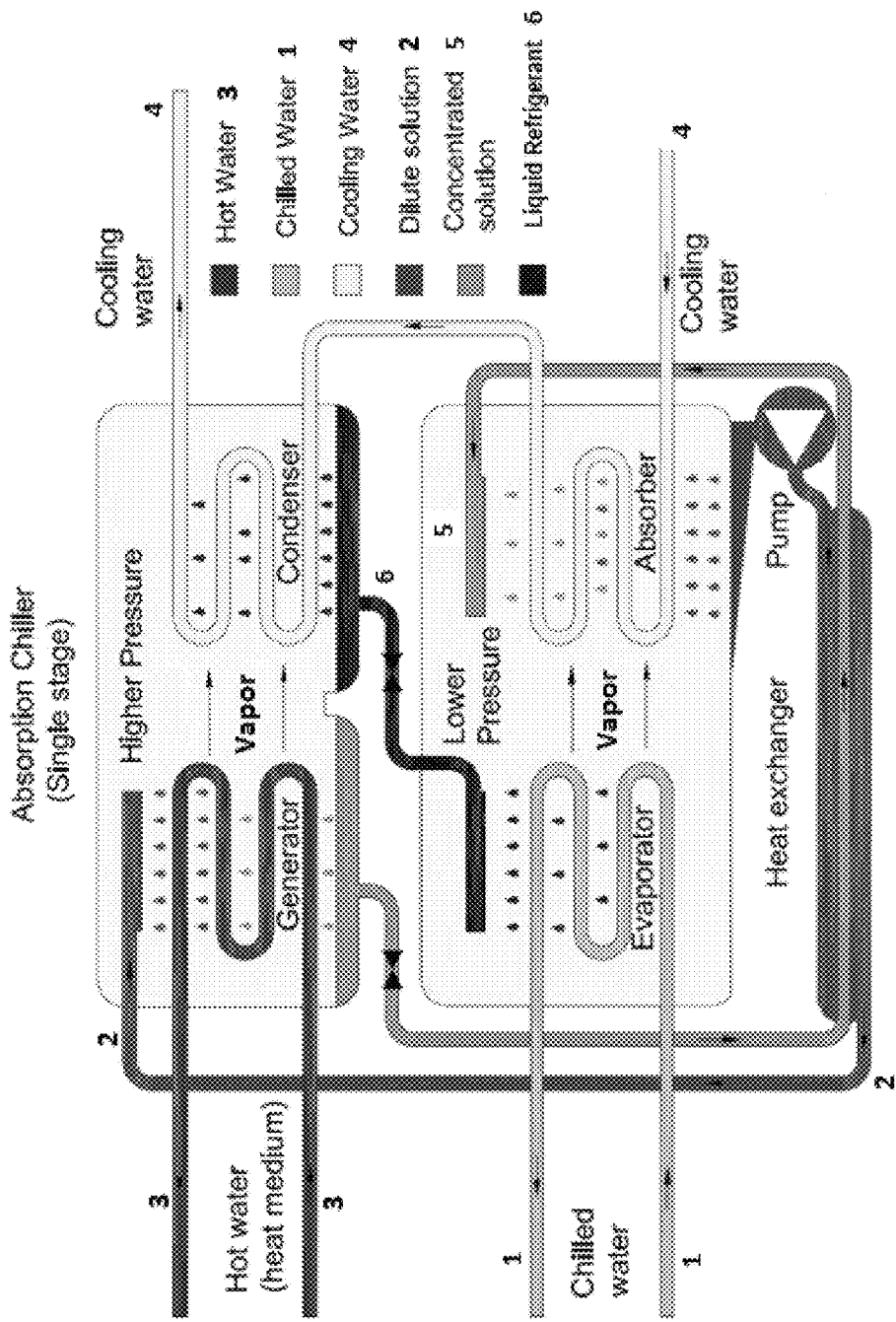
FIG. 1 illustrates an absorption chiller.

FIG. 1 illustrates the schematic of an absorption chiller. An absorption chiller is a machine that utilizes a heat source (e.g., direct flame, hot water, steam, solar energy, waste heat etc.) to drive a cooling process. A mixture of a refrigerant and an absorbent is present in the absorber compartment and the generator compartment of the system.

The present invention relates to a mixture of a refrigerant and a eutectic mixture of two ionic liquids and the use of the mixture in an absorption chiller. The present invention provides an absorption chiller comprising an absorber compartment and a generator compartment, wherein both compartments comprise a mixture of a refrigerant and a eutectic mixture of two ionic liquids as an absorbent.

In the absorption chiller of the present invention, a working pair comprises an absorbent, which is paired (dissolved) with a liquid refrigerant. A refrigerant is a liquid compound used to undergo evaporation in the evaporator compartment of an absorption chiller to produce a chilling effect. A refrigerant in general has appropriate properties for use in such a system, such as low melting point, low-to-medium boiling point, low toxicity, low flammability, low corrosivity, low viscosity, high thermal conductivity, high wettability, and high heat of evaporation. An absorbent has the role of absorbing the refrigerant vapor in the absorber compartment and transferring the refrigerant from a vapor phase to a liquid phase. The generator compartment has the sole role of transferring a portion of the refrigerant from the liquid phase (in solution with the absorbent) to the vapor phase (partial evaporation), thereby performing a vapor-liquid separation procedure. A pure refrigerant is needed for chilling purposes in the evaporator compartment, and therefore, needs to be evaporated from the liquid solution containing the absorbent. The absorbent material generally has a negative role in the generator compartment, since it decreases the vapor pressure of the refrigerant, hindering its evaporation. However, the existence of absorbent in the generator compartment cannot be avoided due to the fact that it is dissolved in the refrigerant stream (working pair solution) incoming from the absorber compartment. An absorption-refrigeration cycle can be accurately modeled using fundamental thermodynamics.

Water is a preferred refrigerant because it is cheap and readily available. Water is non-toxic, non-flammable, and non-explosive, and has a relatively high liquid range. Water also has an exceptionally high enthalpy of vaporization and specific heat capacity. Due to this combination of properties, water is a good heat transfer medium for heat exchange purposes.

However, despite the general suitability of water as a refrigerant in commercial absorption chillers, it is still desirable that the operating pressure and temperature of these systems be reduced, preferably near or at atmospheric conditions. In this case an organic compound possessing aforementioned properties may be used instead. Ethanol is another example of a refrigerant which can be used in the present invention, having higher volatility than water, which may allow system operation closer to atmospheric pressure and temperature.

A eutectic mixture of chemical compounds is generally defined as a mixture of two chemical substances which do not interact to form a third chemical component but, at a certain ratio, inhibit the crystallization process of one another resulting in a system having a lower melting point than either of the individual components. A eutectic mixture of two components may be achieved at a certain concentration ratio of these components. The eutectic mixtures of compounds are generally desired for their lower crystallization temperatures, thereby expanding the liquid range. In eutectic mixtures, the two components will crystallize at the same time (i.e., as if it were a single substance), without undergoing a phase separation in which one component partially crystallizes and partially remains in solution with the other component. The phase diagram of a eutectic mixture of compounds will not show regions having one of the constituents present as a solid phase while the other constituent is still dissolved in a liquid phase, as in the case of non-eutectic mixtures of two or more compounds.

An ionic liquid (IL) is a multi-atomic salt with organic or inorganic cations and anions, usually defined as having a melting temperature of 100° C. or lower. In a eutectic mixture of two ionic liquids ($IL_1$ and $IL_2$), ions from the two compounds are randomly distributed, and the mixture exhibits the solid-liquid phase change behavior of a single substance (i.e. the two components in the eutectic mixture melt or solidify together) without a phase separation. One benefit of a eutectic mixture is that its melting point is lower than the melting point of its constituents. An absorbent with a low melting point is desired to lower the risk of crystallization in the absorption chiller systems.

Many ionic liquids (ILs) are not strongly hydrophilic due to the organic nature of their cations, the larger size of both their cations and anions compared to water molecules, and the limited amount of mass-based solubility of water in ionic liquids due to their relatively large molecular weight. This renders most ILs unsuitable to use as absorbents with water as the refrigerant in an absorption chiller, and the identification of suitable ILs for this purpose is not a simple task.

For example, 1-butyl-3-methylimidazolium bis[(trifluoromethyl)sulfonyl]imide, ($[Bmim]^+[Tf2N]^-$), is a well-known ionic liquid with a molecular weight of 419.4 g/mol. The high molar mass of this ionic liquid means that an equimolar solution with water (1:1), in which 1 mole of ionic liquid is dissolved in 1 mole of water, is equivalent to a solution with only 4.11% by mass of water. In this case, the "working pair" of Bmim Tf2N (absorbent) and water (refrigerant) contains an insufficient amount of refrigerant (water) to be of practical use in absorption chillers.

Instead of using a single IL, the inventors select suitable ionic liquids to form a eutectic mixture to be used as absorbent in an absorption chiller based on the following criteria. At least one of the ionic liquids should be a good water absorbent. The final mixture of the eutectic mixtures of ionic liquids (EMIL) and water (i.e., the "working pair" of absorbent and refrigerant) should have sufficiently low viscosity such that the circulation of the absorbent-refrigerant mixture within the system does not create an unreasonable strain on the system components. The crystallization temperature of the EMIL in the refrigerant should be lower than the temperature of the working temperature range of the absorption chiller to avoid the crystallization of EMIL in the system. At least one of the ionic liquids for use in a eutectic mixture in absorption chillers should have low viscosity and high solvency power towards the refrigerant of interest.

In absorption chillers, the mass basis concentration of the refrigerant (e.g. water) in the absorbent-refrigerant mixture needs to be reasonably high. Therefore, suitable ionic liquids for the present invention in general have low molecular weights, preferably lower than 350 g/mol, and more preferably lower than 250 g/mol.

Two ionic liquids that are suitable to form a eutectic mixture will generally have similar values for enthalpy of fusion (melting). In one embodiment, the two ionic liquids in a eutectic mixture have enthalpies of fusion within 20 kJ/mol, or 15 kJ/mol, or 10 kJ/mol of each other.

Moreover, two ionic liquids (IL1 and IL2) that have identical or similar cations (e.g., cations of IL1 and IL2 are imidazolium, cations of IL1 and 112 are guanidinium, etc.) or similar anions (e.g., anions of IL1 and IL2 are bromide, anions of IL1 and IL2 are chloride, anions of IL1 and IL2 are acetate, anions of IL1 and IL2 are dimethylphosphate, etc.), are more inclined to form a eutectic mixture. In addition, cations and anions of ionic liquids (IL1 and IL2) having dissimilar sizes between their constituent ions are typically more likely to be paired with the counterions from another ionic liquid, forming a eutectic mixture at a certain concentration ratio (e.g., cation of IL1 is dissimilar in size compared to anion of IL1 and/or cation of IL2 is dissimilar in size compared to anion of IL2; or cation of IL1 is dissimilar in size compared to cation of IL2 and/or anion of IL1 is dissimilar in size compared to anion of IL2).

In one embodiment, one or both ionic liquids in a eutectic mixture have dissimilar sizes of anions and cations. For multiatomic or monatomic cations and anions, Van der Waals radius is used as an approximate yet well-accepted measure of the size. For the formation of eutectic mixtures of ionic liquids, it is preferable to have dissimilar sizes of cations and anions in each ionic liquid. The inventors have discovered that a ratio of the size of anion to the size of cation or vice versa is preferably at least 1.5.

For example, in the case of the eutectic mixture of hexamethylguanidinium acetate (IL1) and hexamethylguanidinium dicyanamide (DCA), the Van der Waals radius of the cation, which is the same for both ionic liquids, is ~0.82 nm, and the size of acetate and dicyanamide anions were calculated to be 0.507 nm and 0.52 nm, respectively. For hexamethylguanidinium acetate (IL1) the ratio of the size of cation to the size of anion is 1.615 and for hexamethylguanidinium dicyanamide (DCA) this ratio is 1.57.

The eutectic mixture of ionic liquids suitable for use as an absorbent in a water-based absorption chiller (i.e. with water as the refrigerant) has a high hygroscopic effect comparable to that of LiBr. The mixture of the eutectic mixture of ionic liquids with water in the absorbent-refrigerant working pair has a reasonably low viscosity, and the eutectic mixture exhibits a lower risk of crystallization due to its lower melting point.

The eutectic mixture of the present invention typically has a melting point ($T_m$) 10 to 30° C. lower than the $T_m$ of each of the two individual ionic liquids in their pure form. The eutectic mixture of the present invention typically has a melting point ($T_m$) lower than 300 K (27° C.), preferably lower than 290 K (17° C.), and more preferably lower than 273 K (0° C.). For example, the melting point of a eutectic mixture of the present invention is between 250 K and 290 K for a water-based absorption chiller.

The eutectic mixture of the present invention when mixed with a proper amount of refrigerant such as water typically has a kinematic viscosity less than 15 centistokes, preferably less than 10 centistokes.

Table 1 provides examples of eutectic mixtures of ionic liquids ($IL_1$ and $IL_2$) suitable for use in water-based and/or ethanol-based absorption chillers.

The eutectic point of two ionic liquids is mainly a function of the properties of the individual ionic liquids. In normal situations in which the refrigerant does not react or otherwise influence the eutectic mixture of ionic liquids, the type of refrigerant chosen would not affect the eutectic temperature and eutectic composition.

The inventors have discovered that hygroscopic ionic liquids with low molecular weight can resolve the issue of limited (mass-based) water solubility of ionic liquids. For example, cations with a high degree of water tendency (e.g. guanidinium-based cations) can first be functionalized by the addition of appropriate functional groups having the desired properties. They can then be combined with a desired anion such as acetate, which exhibits ultra-high hygroscopic effects and low melting point, to create a new absorbent with desired properties.

Effective eutectic mixtures of ionic liquids can be designed based on quantum chemistry calculations and thermodynamic-based models, and then synthesized so that the final absorbent has a desirable melting point lower than those of the separate individual ionic liquids. The eutectic mixture can inherit its desired thermodynamic properties (e.g. high tendency towards water) from one of its components; for example, guanidinium-based acetate ionic liquids, and its desired physical properties (e.g. low viscosity) from the other component, for example, guanidinium-based dicyanamide ionic liquids.

The following examples further illustrate the present invention. These examples are intended merely to be illustrative of the present invention and are not to be construed as being limiting.

EXAMPLES

The thermo-dynamic COP (Coefficient of Performance) of an absorption chiller is defined as the amount of cooling load generated in the evaporator, $Q_E$, (in kilowatt [kW]) divided by the amount of thermal/heat energy, $Q_G$, (in kilowatt [kW]) used to heat up the dilute solution in the generator in order to release refrigerant vapor. A high COP is desirable meaning that for a given expense being paid (thermal energy being used), more work (cooling load) is being delivered. The COP however does not take into account the quality or cost of the thermal/heat energy $Q_G$ used.

The thermodynamic ECOP (Exergetic COP) takes the quality of heat being used into consideration.

$$ECOP = COP \cdot \frac{\left(\frac{T_0}{T_E} - 1\right)}{\left(1 - \frac{T_0}{T_h}\right)}$$

Where $T_0$=298 K is the room temperature, $T_E$ the temperature in the evaporator and $T_h=T_G+(5 \text{ to } 10 \text{ K})$ is the heat source temperature, with $T_G$ being the temperature in the generator compartment. [2] Use of waste heat or a thermal stream with a lower temperature (i.e., a lower $T_G$) will eventually increase the ECOP pointing towards a more economical process.

Example 1: Performance Comparison of Guanidinium-Based Ionic Liquids and a Eutectic Mixture In the following example certain thermo-physical properties of hexamethylguanidinium-based ILs, a eutectic mix-

TABLE 1

Examples of eutectic mixtures of ionic liquids

| $IL_1$ | $IL_2$ |
|---|---|
| 1-ethyl-3-methylimidazolium acetate | 1-ethylpyridinium acetate |
| 1-butyl-3-methylimidazolium acetate | 1-butylpyridinium acetate |
| 1-ethyl-3-methylimidazolium dimethylphosphate | 1-ethylpyridinium dimethylphosphate |
| 1-butyl-3-methylimidazolium dimethylphosphate | 1-butylpyridinium dimethylphosphate |
| 1-ethyl-3-methylimidazolium bromide | 1-ethylpyridinium bromide |
| 1-butyl-3-methylimidazolium bromide | 1-butylpyridinium bromide |
| 1-butyl-3-methylimidazolium bromide | 1-ethylpyridinium bromide |
| Tetramethylammonium chloride | 1-ethyl-3-methylimidazolium chloride |
| Tetraethylammonium chloride | 1-ethyl-3-methylimidazolium chloride |
| 1-ethyl-3-methylimidazolium acetate | 1-ethyl-3-methylimidazolium dimethylphosphate |
| 1-butyl-3-methylimidazolium bromide | 1-butyl-3-methylimidazolium chloride |
| hexamethylguanidinium acetate | hexamethylguanidinium dicyanamide | ture of hexamethylguanidinium-based ILs, and LiBr are shown. Example 1 demonstrates that the properties of a eutectic mixture of ILs are advantageous compared to those of a single IL. Further, the absorptive properties of the eutectic are advantageous compared to that of LiBr as crystallization is avoided due to the low melting point of the eutectic mixture of ILs. Moreover, the presented ILs and eutectic mixture of the ILs in water are less corrosive working pairs than LiBr in water.

A Continuum Solvation Model (CSM) based on the concept of dielectric constant [3-7] was used to predict the solubility values, the melting point, and the viscosity of hexamethylguanidinium-based ILs and the eutectic mixture of hexamethylguanidinium-based ILs. Ab initio calculations using density functional theory (DFT) were utilized to calculate the molecular structure/geometry along with the electric charge density as an input to the CSM calculations. The results of the computations along with experimental results for LiBr are shown in Table 2.

Table 2 further lists the computed COP and ECOP along with the mass-based concentration of absorbent (Mass % IL) in both dilute and concentrated streams in an absorption chiller working with different guanidinium-based ionic liquids and water as working pairs. Preferably, a eutectic mixture should allow at least a 5% change in the concentration of water between the generator and absorber compartments of an absorption chiller.

Table 2 shows that hexamethylguanidinium acetate ionic liquid can absorb higher amounts of water compared to other ionic liquids listed (better hygroscopic properties). This ionic liquid can be diluted up to the point of having ~18% (wt %) of water in the solution and still be able to operate at the low pressures, at which the evaporator compartment is performing (i.e., 0.01 atm). The absorber and evaporator are interconnected and thus have the same operating pressure. More dilute solutions of hexamethylguanidinium acetate in water could be made. However, water contents of more than 18 wt % generates water vapor pressure higher than 0.01 atm in the absorber, which decreases the cooling quality (performance) of the absorption chiller. This is because at higher pressures of absorber/evaporator, water will evaporate in the evaporator at higher temperatures than the preferable <5° C. 5° C. is at the higher end of an acceptable evaporator temperature in absorption chillers. A low temperature needs to be maintained in the evaporator in order generate a chilled water stream (e.g., with a temperature of 8° C. or lower) suitable for air-conditioning purposes (i.e., ~8° C. or lower). If the temperature of the chilled water stream rises above this level, the efficiency of the absorption chiller is substantially reduced. It is noteworthy that the high amount of water which can be present in the mixture with hexamethylguanidinium acetate, compared to other ILs listed in Table 2, will help as well to decrease the viscosity of the ionic liquid-water (working pair) mixture.

TABLE 2

Comparison of the performance of individual guanidinium-based ionic liquids, the eutectic mixtures, and LiBr as absorbents with water as the refrigerant. Temperatures of evaporator, absorber, and condenser are 5° C., 35° C., and 40° C., respectively.

| Absorbent | COP Predicted | ECOP Predicted | Mass % absorbent (dilute solution*) Predicted | Mass % absorbent (concentrated solution) Predicted | $T_m$ (K) Predicted | Kinematic Viscosity Of the concen. stream @ 60° C. cst Predicted |
|---|---|---|---|---|---|---|
| Hexaethylguanidinium Acetate | 0.769 | 0.304 | 85.9 | 90.9 | 312.75 | 20.88 |
| Hexamethylguanidinium Acetate | 0.768 | 0.314 | 82.2 | 87.2 | 335.3 | 10.84 |
| Hexamethylguanidinium Dicyanamide (DCA) | 0.731 | 0.106 | 94.1 | 99.1 | 316.2 | 6.07 |
| Hexamethylguanidinium DMP | 0.782 | 0.305 | 88.97 | 93.97 | 377.8 | 31.80 |
| Hexamethylguanidinium Tf$_2$n | <<0.7 (N/O[#]) | <<0.3 (N/O) | 98 | 98 + 5 (N/O) | <380 | — |
| LiBr[1] (comparative) | 0.775[exp] | 0.291[exp] | 57[exp] | 62[exp] | 825[exp] | 2.04[exp] |
| Eutectic Mixture: [IL$_1$]: Hexamethylguanidinium Acetate (40 ± 10%) [IL$_2$]: Hexamethylguanidinium Dicyanamide (100 − [IL$_1$] %) | 0.791 | 0.182 | 89 | 94 | 265 ± 15 | 8.64 ± 1.2 |

*"Solution" is a mixture of absorbent (e.g., an IL, a eutectic mixture of ILs, or LiBr) and a refrigerant liquid (e.g., water). A "concentrated solution" has a higher concentration of absorbent than that of a "dilute solution."
[exp]Experimental data;
[#]N/O = Not operable.

As can be seen from Table 2, a large and hydrophobic anion such as bis(trifluoromethylsulfonyl)imide (Tf$_2$N) adversely impacts the performance of the system due to their low tendency for water absorption. Use of hydrophobic ionic liquids in absorption chillers will eventually decrease the water absorption power of the absorbent, significantly. That means that a lower amount of water will be absorbed and then released in a one refrigeration-absorption cycle. This adversely impacts the performance of the system and lowers the overall COP of the absorption chillers.

An example of a eutectic mixture of ionic liquids exhibiting desired properties as an absorbent in an absorption chiller, as shown in Table 2, is a mixture of 40±10% (wt %) hexamethylguanidinium acetate with 60±10% (wt %) hexamethylguanidinium dicyanamide (DCA) ionic liquids. The eutectic mixture has a predicted melting point of 265±15 K, which is significantly lower than the melting point of either hexamethylguanidinium acetate (335.3 K) or hexamethylguanidinium dicyanamide (316.2 K). A lower melting point of the eutectic mixture lowers the risk of crystallization of the absorbent. With the lower melting point of the absorbent (the eutectic mixture), the operating conditions of the absorption chiller can be re-optimized to achieve higher performance indices.

Table 2 also shows that the kinematic viscosity of the mixture of a eutectic mixture of hexamethylguanidinium acetate and hexamethylguanidinium dicyanamide and water in the concentrated stream (8.64±1.2 cst) is lower than the viscosity of the concentrated mixtures of several other individual ionic liquids with water, such as hexaethylguanidinium acetate, hexamethylguanidinium acetate, and hexamethylguanidinium DMP (20.88, 10.84, and 31.80 cst, respectively). By inclusion of a low-viscosity component in the eutectic mixture, in this case hexamethylguanidinium dicyanamide, the efficiency of the absorption chilling process is substantially improved, by lowering the pumping energy needed.

In summary, the eutectic mixture of hexamethylguanidinium acetate and hexamethylguanidinium dicyanamide can be used as a less corrosive absorbent in an absorption chiller using water as a refrigerant. This eutectic mixture exhibits a low melting point, lower than that of either pure hexamethylguanidinium acetate or hexamethylguanidinium dicyanamide. The low melting point is beneficial in avoiding crystallization of the absorbent. In the eutectic mixture, the acetate anion is beneficial from the thermodynamics point of view since it can increase the water absorption power and dicyanamide anion is beneficial from the physical properties point of view since it can decrease the viscosity.

Example 2: Comparison on the Performance of Two Ionic Liquids and their Eutectic Mixture with a Non-Water Refrigerant (i.e. Ethanol)

This example shows how the eutectic mixture of two bromide-based ionic liquids, 1-butyl-3-methylimidazolium bromide (Bmim Br) and 1-ethylpyridinium bromide (EPy Br) can be advantageously used as an absorbent with ethanol as a refrigerant.

Here, existence of the same small monoatomic bromide (Br⁻) anion in the ionic liquids helps the formation of a eutectic mixture.

Figure 2:
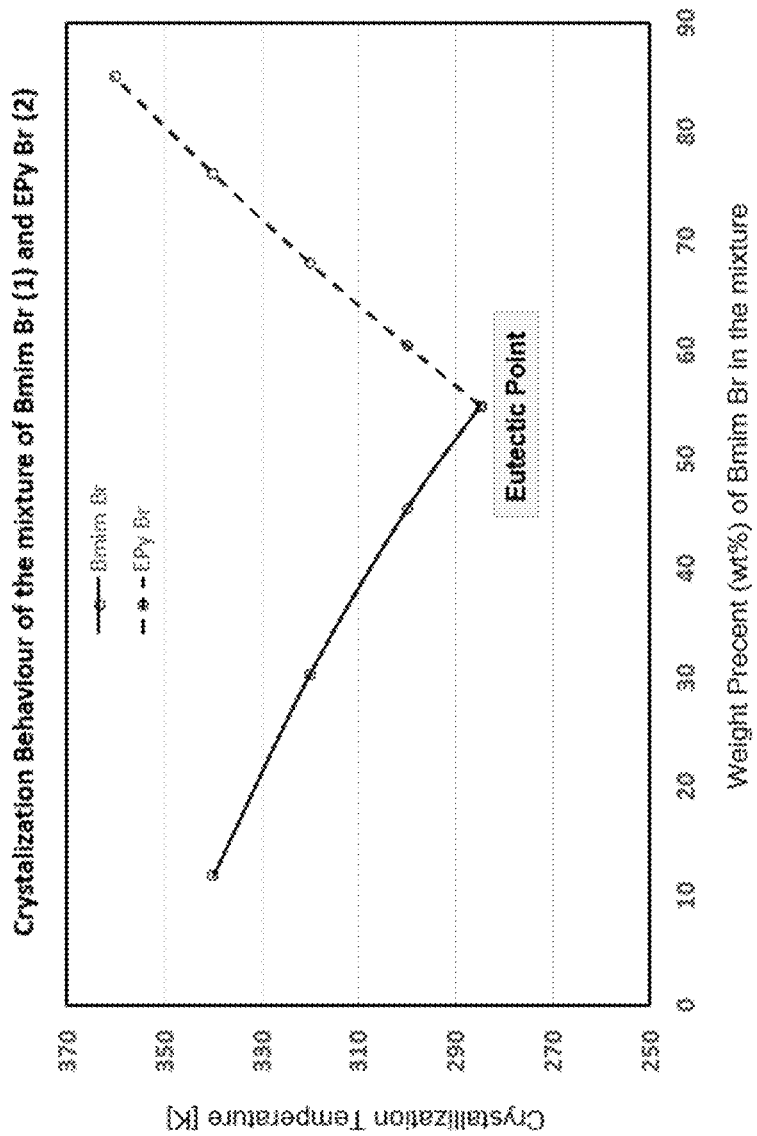
FIG. 2 shows the crystallization behavior of a mixture of two ionic liquids, Bmim Br and EPy Br.

As shown in FIG. 2 by computational analysis, the eutectic point occurs at a composition of 55 wt % Bmim Br and 45 wt % EPy Br in the solution with a melting temperature, $T_m$, of 285K. The melting point of the ionic liquids mixture at the eutectic point is significantly lower than that of each ionic liquid individually, listed in Table 3 below.

TABLE 3

Properties of ionic liquids Bmim Br, Epy Br, and their eutectic mixture

| Ionic Liquids | Melting Point [K] | Heat of Fusion [kJ/mol] |
|---|---|---|
| Bmim Br | 351 | 22.9 |
| EPy Br | 391.3 | 12.8 |
| Eutectic Mixture (55% Bmim Br) | 285 | 17.7 |

After showing the feasibility of the formation of the eutectic mixtures of bromide-based ionic liquids, the crystallization behavior of this eutectic mixture in ethanol refrigerant was calculated.

Figure 3:
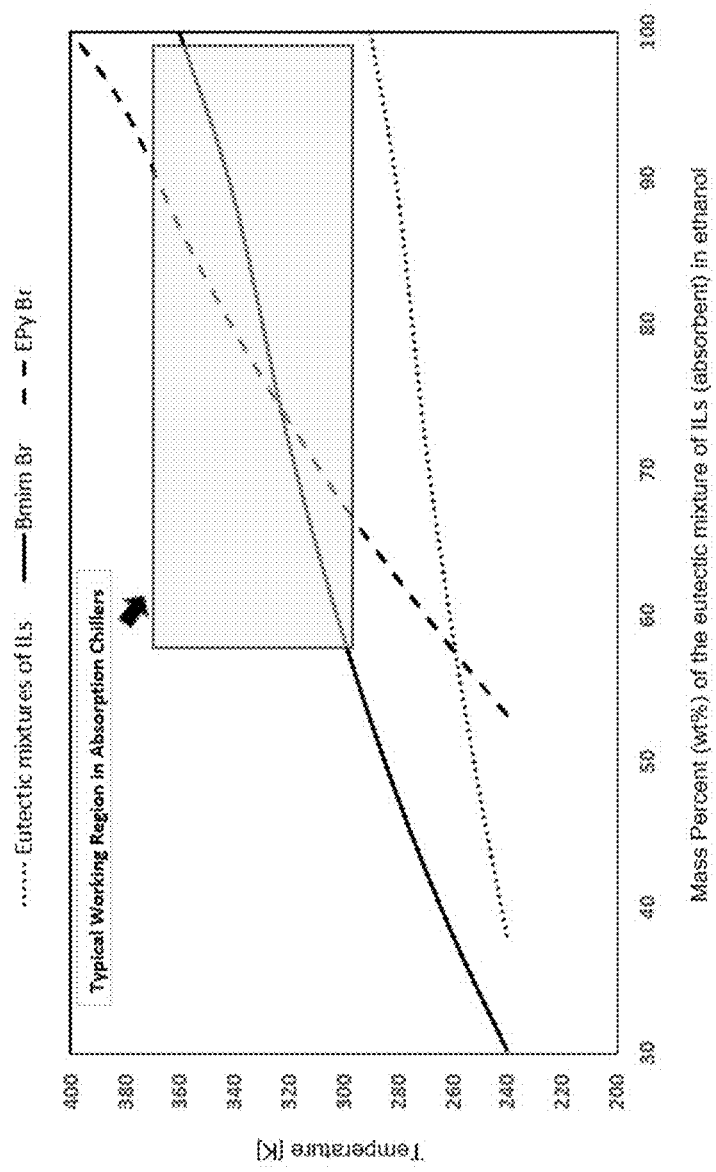
FIG. 3 shows the crystallization temperature vs. mass percent of the pure Bmim Br, pure EPy Br, and the eutectic mixture of the two ionic liquids in the ethanol refrigerant.

FIG. 3 shows the crystallization temperature (K) vs. the mass fraction of absorbent (the eutectic mixture of Bmim Br and EPy Br) in an ethanol refrigerant. As seen in FIG. 3, the crystallization temperature of the eutectic mixture of these two bromide based ionic liquids is significantly lower than the crystallization point of each individual ionic liquid (in their pure form) when dissolved in ethanol. At the typical concentrations of absorbent in the absorption chillers (about >60 wt % or >0.6 mass fraction), the crystallization point of the eutectic mixture is between 10 and 40° C. lower than that of the pure ionic liquids in ethanol refrigerant. FIG. 3 shows that the crystallization curve of the solution of the absorbent (the eutectic mixture) in the refrigerant is outside the working temperature region of an absorption chiller. This is desirable because no crystallization will occur within the system.

Example 3: Synthesis of Hexamethylguanidinium Acetate

The synthesis of N,N,N',N',N'',N''-hexamethylguanidinium acetate (6MeGuaOAc) was accomplished through a three-step protocol.

Figure 4:
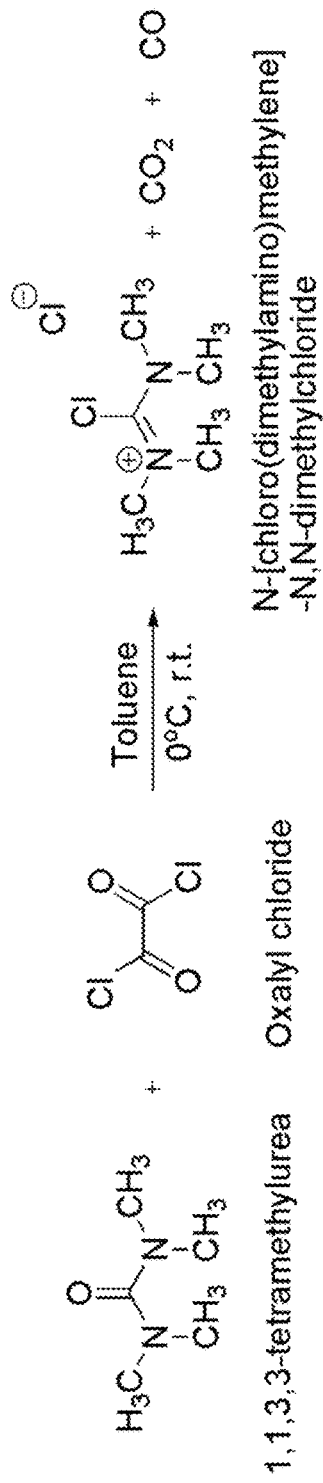
FIG. 4 shows the reaction scheme for synthesis of N-[chloro(dimethylamino)methylene]-N,N-dimethylchloride (4MeUCl) from 1,1,3,3-tetramethylurea (4MeUrea) and oxalyl chloride (OxalylCl).

I. In the first step, 1,1,3,3-tetramethylurea (4MeUrea) was converted to N-[chloro(dimethylamino)methylene]-N,N-dimethylchloride (4MeUCl). This reaction was performed under completely moisture-free conditions by necessity. UHP argon was used to provide an inert atmosphere. As shown in FIG. 4, 1,1,3,3-tetramethylurea, in presence of 1:5 excess amount of oxalyl chloride added dropwise at 0° C., generated 4MeUCl.

6.44 mL of 1,1,3,3-tetramethylurea (99%, d=0.969 g/mL) and 40 mL toluene were added to a three-neck round bottom (3rb) flask and left for 15 minutes under stirring to reach the ice bath temperature.

23.18 mL of oxalyl chloride were slowly added to the three-neck flask with an automated syringe at a rate of 0.01 mL/min. After the addition was finished, the ice-bath was removed and the mixture was left to stir for 24 hours at room temperature.

A slightly yellow solid product was formed. The flask was then taken off the condenser and the solvent (i.e. toluene) and the excess amount of oxalyl chloride were removed in vacuo with the rotary evaporator set at 55° C. and 25 mbar. The intermediate was left under high vacuum to fully dry for 48 hours.

Figure 5:
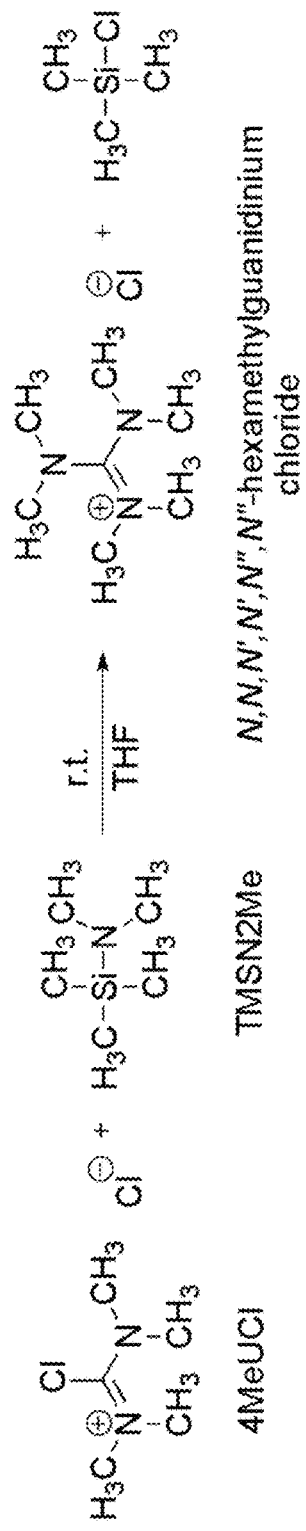
FIG. 5 shows the reaction scheme for synthesis of N,N,N',N',N'',N''-hexamethylguanidinium chloride (6MeGuaCl) from 4MeUCl in presence of 1:2 excess N,N-dimethyltrimethylsilylamine (TMSN2Me), using extra-dry THF as solvent.

II. In the second step, 4MeUCl was converted to N,N,N',N',N'',N''-hexamethylguanidinium chloride (6MeGuaCl) in presence of 1:2 excess N,N-dimethyltrimethylsilylamine (TMSN2Me), using extra-dry THF as solvent, as shown in FIG. 5.

4.81 g of 4MeUCl (99%) and 80 mL tetrahydrofuran (THF) were added to a three-neck round bottom (3rb) flask and left for 15 minutes under stirring to reach the ice bath temperature.

9.30 mL (97%, d=0.723 g/cm3) of N,N-dimethyltrimethylsilylamine (TMSN2Me) were slowly added to the three-neck flask with an automated syringe at a rate of 0.2 mL/min. After the addition was finished, the ice-bath was removed and the mixture was left to stir for 1 hour at room temperature and another 2 hours at 35° C.

The crude product, a light yellow liquid, was then processed in a rotary evaporator at 55° C. and 25 mbar for 1 hour and then kept under high vacuum for another 24 hours to fully remove any trace amount of solvent. The by-product TMS-Cl, with a boiling point of 57° C., was removed during this procedure, a chromatographic purification not being further required.

Figure 6:
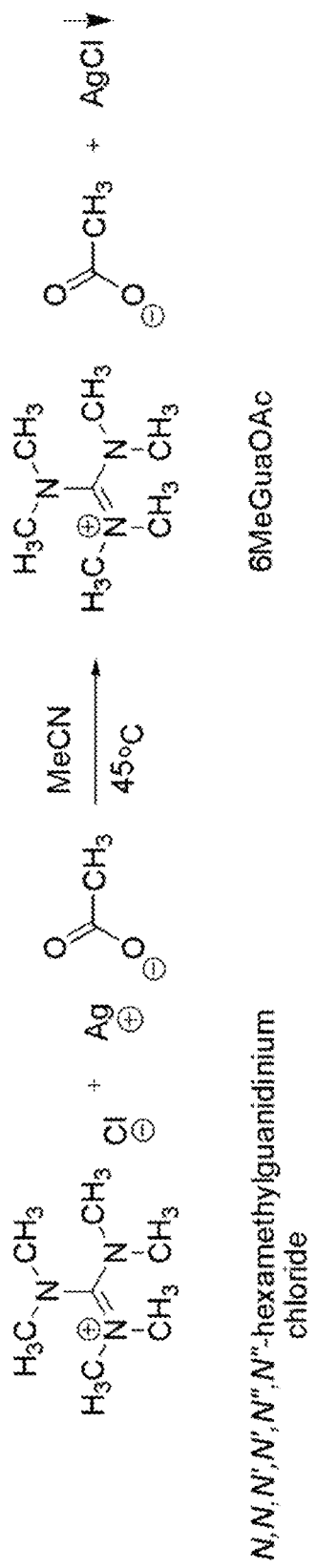
FIG. 6 shows the reaction scheme for synthesis of N,N,N',N',N'',N''-hexamethylguanidinium acetate (6MeGuaOAc) from 6MeGuaCl via a metathesis reaction in presence of equimolar amount of silver acetate.

III. In the third step, 6MeGuaOAc was synthesized from 6MeGuaCl via a metathesis reaction in presence of equimolar amount of silver acetate, as shown in FIG. 6.

9.24 g of 6MeGuaCl (99%) and 8.58 g of AgOAc (99%, photosensitive) were charged to a round bottom (rb) flask. To the rb flask, 150 mL of acetonitrile (ACS grade) were added and then the setup was connected to a Schlenk line and wrapped in aluminum foil. The mixture was left to stir for 24 hours at 45° C. After stirring, the hotplate was turned off and left 15 minutes for phase separation. AgCl separated out as a gray precipitate on the bottom of the rb flask. The slurry was gravitationally filtered through two filter papers. The solvent was removed in vacuo with the rotary evaporator set at 55° C. and 25 mbar. 100 mL of acetone were added to the rb and the flask was stored at low temperature to further allow precipitation of AgCl by-product and then vacuum filtrated. This cycle was repeated multiple times until no AgCl was detected. The final product comprising 6MeGuaOAc was left under high vacuum to fully dry for 48 hours.

It is to be understood that the foregoing describes preferred embodiments of the present invention and that modifications may be made therein without departing from the scope of the present invention as set forth in the claims.

REFERENCES

[1] Zhang, X., & Hu, D. (2011). Performance simulation of the absorption chiller using water and ionic liquid 1-ethyl-3-methylimidazolium dimethylphosphate as the working pair. *Applied Thermal Engineering*, 31(16), 3316-3321.

[2] Al-Tahaineh, H., Frihat, M., and Al-Rashdan, M. (2013). Exergy Analysis of a Single-Effect Water-Lithium Bromide Absorption Chiller Powered by Waste Energy Source for Different Cooling Capacities. *Energy and Power* 3(6), 106-118.

[3] Klamt, A., & Schüürmann, G. J. G. J. (1993). COSMO: a new approach to dielectric screening in solvents with explicit expressions for the screening energy and its gradient. *Journal of the Chemical Society, Perkin Transactions* 2, (5), 799-805.

[4] Klamt, A., (1995). Conductor-like screening model for real solvents: a new approach to the quantitative calculation of solvation phenomena. *The Journal of Physical Chemistry*, 99(7), 2224-2235.

[5] Eckert, F., & Klamt, A. (2002). Fast solvent screening via quantum chemistry: COSMO-RS approach, *AIChE Journal*, 48(2), 369-385.

[6] Tomasi, J., Mennucci, B., & Cammi, R. (2005). Quantum mechanical continuum solvation models. *Chemical reviews*, 105(8). 2999-3094.

[7] Klamt, A., Eckert, F., Hornig, M., Beck, M. E., & Bürger, T. (2002). Prediction of aqueous solubility of drugs and pesticides with COSMO-RS. *Journal of computational chemistry*, 23(2), 275-281.

What is claimed is:

1. An absorption chiller comprising a mixture of a refrigerant and an absorbent, and the absorbent is a eutectic mixture of two ionic liquids selected from the group consisting of:
   1-ethyl-3-methylimidazolium acetate and 1-ethylpyridinium acetate,
   1-butyl-3-methylimidazolium acetate and 1-butylpyridinium acetate,
   1-butyl-3-methylimidazolium dimethylphosphate and 1-butylpyridinium dimethylphosphate,
   1-ethyl-3-methylimidazolium acetate and 1-ethyl-3-methylimidazolium dimethylphosphate,
   1-ethyl-3-methylimidazolium dimethylphosphate and 1-ethylpyridinium dimethylphosphate,
   1-ethyl-3-methylimidazolium bromide and 1-ethylpyridinium bromide,
   1-butyl-3-methylimidazolium bromide and 1-butylpyridinium bromide,
   1-butyl-3-methylimidazolium bromide and 1-ethylpyridinium bromide,
   tetramethylammonium chloride and 1-ethyl-3-methylimidazolium chloride,
   tetraethylammonium chloride and 1-ethyl-3-methylimidazolium chloride,
   1-butyl-3-methylimidazolium bromide and 1-butyl-3-methylimidazolium chloride, and
   hexamethylguanidinium acetate and hexamethylguanidinium dicyanamide;
   wherein the concentration ratio of the two ionic liquids in the eutectic mixture is the concentration ratio at the eutectic point of the eutectic mixture.

2. The absorption chiller of claim 1, wherein the refrigerant is water or ethanol.

3. The absorption chiller of claim 1, wherein the eutectic mixture has a melting point of 290 K or less.

4. The absorption chiller of claim 1, wherein the mixture of the refrigerant and the eutectic mixture has a viscosity lower than 15 centistokes.

5. The absorption chiller of claim 1, wherein the two ionic liquids have enthalpies of fusion within 20 kJ/mol.

6. The absorption chiller of claim 1, wherein the two ionic liquids have melting points within 50K.

7. The absorption chiller of claim 1, wherein the two ionic liquids have the same cation.

8. The absorption chiller of claim 7, wherein the cation is imidazolium or guanidinium.

9. The absorption chiller of claim 8, wherein the two ionic liquids are hexamethylguanidinium acetate and hexamethylguanidinium dicyanamide.

10. The absorption chiller of claim 1, wherein the two ionic liquids have the same anion.

11. The absorption chiller of claim 10, wherein the anion is bromide, chloride, acetate, or dimethylphosphate.

12. The absorption chiller of claim 1, wherein the two ionic liquids are selected from the group consisting of:
   1-ethyl-3-methylimidazolium acetate and 1-ethylpyridinium acetate;
   1-butyl-3-methylimidazolium acetate and 1-butylpyridinium acetate;
   1-butyl-3-methylimidazolium dimethylphosphate and 1-butylpyridinium dimethylphosphate; and
   1-ethyl-3-methylimidazolium acetate and 1-ethyl-3-methylimidazolium dimethylphosphate.

13. The absorption chiller of claim 1, wherein the two ionic liquids in the eutectic mixture melt or solidify at the same time without undergoing a phase separation.

14. The absorption chiller of claim 1, wherein the crystallization temperature of the eutectic mixture is lower than that of either of the two individual ionic liquids.

* * * * *